United States Patent [19]

Doddi et al.

[11] 4,052,988

[45] Oct. 11, 1977

[54] SYNTHETIC ABSORBABLE SURGICAL DEVICES OF POLY-DIOXANONE

[75] Inventors: Namassivaya Doddi; Charles C. Versfelt, both of Somerville; David Wasserman, Springfield, all of N.J.

[73] Assignee: Ethicon, Inc., Somerville, N.J.

[21] Appl. No.: 648,236

[22] Filed: Jan. 12, 1976

[51] Int. Cl.² .............................................. A61L 17/00
[52] U.S. Cl. .......................................... 128/335.5; 3/1;
  128/92 B; 128/92 D; 260/78.3 R
[58] Field of Search ............................... 128/335.5, 92;
  260/78.3; 3/1

[56] References Cited

U.S. PATENT DOCUMENTS

| 3,063,967 | 11/1962 | Schultz | 260/78.3 |
|---|---|---|---|
| 3,063,968 | 11/1962 | Schultz | 260/78.3 |
| 3,190,858 | 6/1965 | Cox et al. | 260/78.3 |
| 3,297,033 | 1/1967 | Schmitt et al. | 128/335.5 |
| 3,636,956 | 1/1972 | Schneider et al. | 128/335.5 |
| 3,645,941 | 2/1972 | Snapp et al. | 260/78.3 |
| 3,867,190 | 2/1975 | Schmitt et al. | 128/335.5 X |
| 3,960,152 | 6/1976 | Augurt et al. | 128/335.5 |

OTHER PUBLICATIONS

Palomaa et al.-Ber. Deut. Chem. Gesellsch., vol. 66B, pp. 1629-1632 (1933).

*Primary Examiner*—Dalton L. Truluck
*Attorney, Agent, or Firm*—Wayne R. Eberhardt

[57] ABSTRACT

Synthetic absorbable sutures and other surgical devices are prepared from polymers of p-dioxanone and 1,4-dioxepan-2-one, and alkyl substituted derivatives thereof. Monofilament sutures of oriented fibers are characterized by good tensile and knot strength and a high level of flexibility and softness. The sutures have good in vivo strength retention and are slowly absorbed without significant tissue reaction.

39 Claims, 5 Drawing Figures

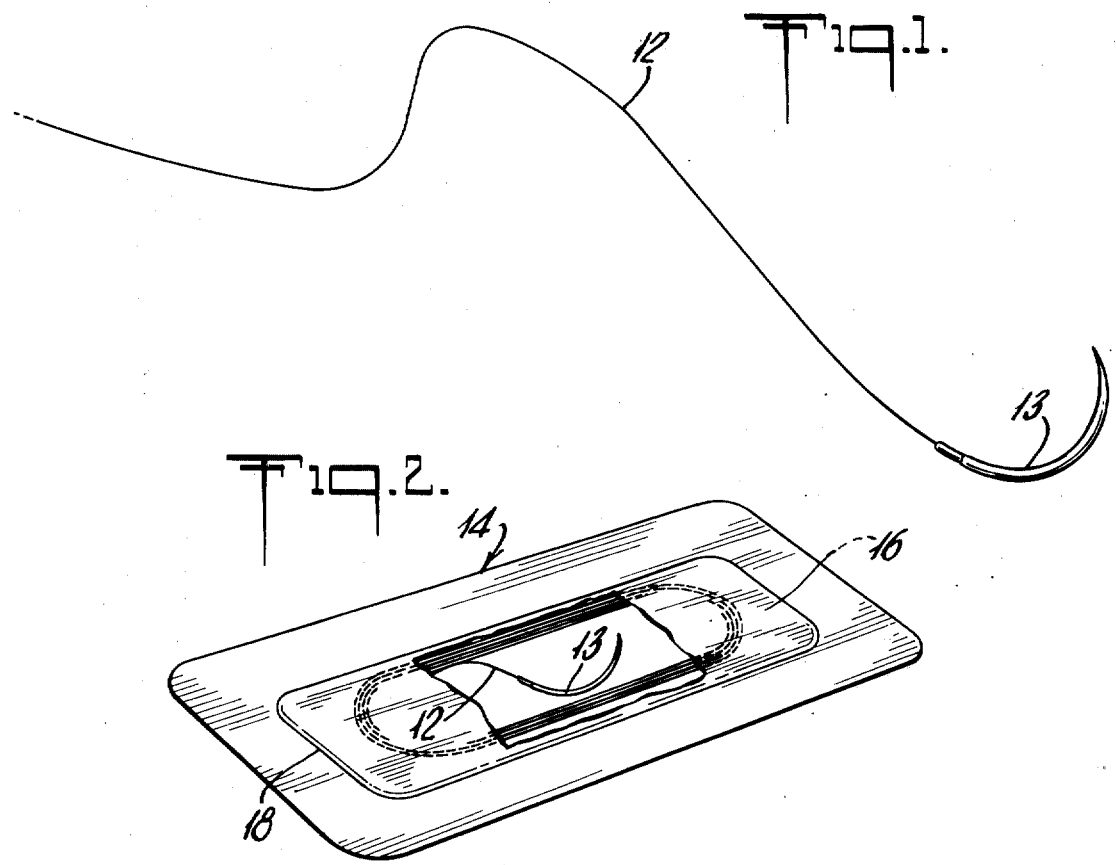
Fig.1.
Fig.2.
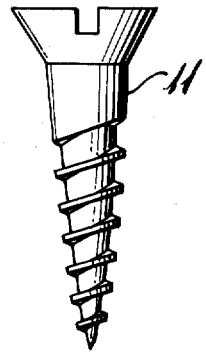
Fig.3.
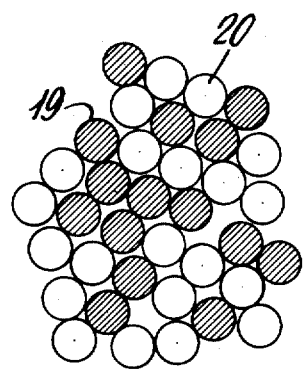
Fig.4.
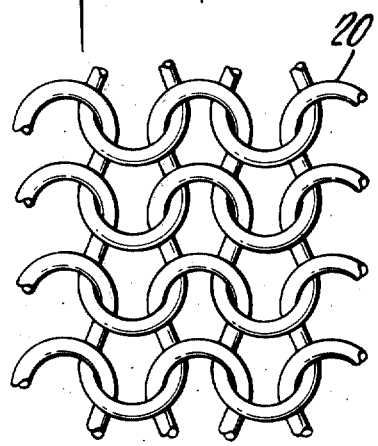
Fig.5.

SYNTHETIC ABSORBABLE SURGICAL DEVICES OF POLY-DIOXANONE

BACKGROUND OF THE INVENTION

1. Field of the Invention

This invention relates to synthetic absorbable sutures, and more particularly, to synthetic absorbable sutures comprising extruded and oriented filaments of polymers of p-dioxanone or 1,4-dioxepan-2-one.

2. Description of Prior Art

Absorbable suture materials have traditionally been natural collagenous materials obtained from sheep or beef intestine, commonly known as catgut. More recently, it has been proposed to manufacture synthetic absorbable sutures from polyesters of hydroxycarboxylic acids, notably polylactide, polyglycolide, and copolymers of lactide and glycolide. Such synthetic absorbable sutures are described in U.S. Pat. Nos. 3,636,956, 3,297,033 and elsewhere in the literature.

Among the requirements of an ideal absorbable suture are that it should have good handling properties, should approximate and hold tissue for proper healing with minimal tearing and tissue damage, should have adequate straight tensile and knot strength, should be controllably uniform in properties including dimensional stability within the body, should be sterilizable, should be absorbable by living tissue, preferably at a constant rate regardless of the place in the body or the condition of the patient, without causing such unfavorable tissue reactions as walling off, granuloma formation, excessive edema, etc., and finally should be capable of being properly and easily tied into surgical knots.

While multifilament sutures manufactured from polymers of lactide and glycolide fulfill the above requirements to a large degree, monofilament sutures of these materials are considerably less flexible than catgut and these synthetic sutures are accordingly generally limited to a multifilament, braided construction. Sutures of glycolide polymers are also not suitable for sterilization by radiation without suffering severe degradation of physical properties.

The present invention provides synthetic absorbable sutures having a high degree of softness and flexibility which allows the sutures to be used in monofilament form. The sutures can also be sterilized with cobalt 60 radiation without serious loss of suture strength. It is accordingly an object of the present invention to provide synthetic absorbable sutures having unique and desirable properties not available with the sutures of the prior art.

We have discovered that polymers of p-dioxanone and 1,4-dioxepan-2-one prepared from monomers of very high purity can be melt extruded into pliable, monofilament fibers which are slowly absorbed in animal tissue without significant adverse tissue reaction. The fibers have good tensile and knot strength and good in vivo strength retention, and can be sterilized with cobalt 60 without serious loss of these properties.

Polymers of p-dioxanone and fibers extruded therefrom have been known in the art. U.S. Pat. Nos. 3,063,967 and '968 for example, describe the polymerization of p-dioxanone and the preparation of films and fibers therefrom. The low tensile strength of fibers prepared in accordance with the teachings of these references, however, make these fibers generally unsuitable for use as surgical sutures. Moreover, there was no appreciation in these references of the absorbability of such fibers which were reported to be resistant to the effects of saline and distilled water.

Other references dealing with the polymerization of p-dioxanone include, but are not limited to, U.S. Pat. Nos. 3,190,858, 3,391,126 and 3,645,941 which disclose various catalysts for the polymerization of lactones such as p-dioxanone, and U.S. Pat. No. 3,020,289 which describes the polymerization of p-dioxanone in the presence of sulfuric acid. None of these references suggest polymers of p-dioxanone or 1,4-dioxepan-2-one for use in the preparation of synthetic absorbable sutures in accordance with the present invention.

SUMMARY

Synthetic absorbable sutures are prepared from polymers of monomers having the formula:

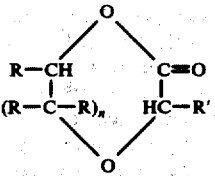

wherein R' and each R are hydrogen, methyl or ethyl and n is 1 or 2, provided that when n is 2, at least two R groups are hydrogen.

Polymers prepared by the polymerization of very pure monomers are melt extruded into filaments suitable for use as synthetic absorbable sutures. The filaments are characterized by high tensile and knot strength, good strength retention in vivo, and a Young's modulus of less than about 600,000 psi corresponding to a high degree of softness and flexibility.

DESCRIPTION OF DRAWINGS

FIG. 1 is a perspective view of a needle-suture combination;

FIG. 2 is a perspective view of a suture-needle combination within a hermetically sealed container;

FIG. 3 illustrates a screw machined from the polymer of the present invention;

FIG. 4 is a cross-sectional view of a composite yarn containing filaments of different composition and;

FIG. 5 is a plan view of a surgical fabric knitted from fibers of the present invention.

DESCRIPTION OF PREFERRED EMBODIMENTS

Polymers of the present invention are comprised of units having the general formula:

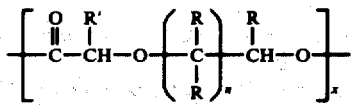

wherein R' and R are individually hydrogen, methyl, or ethyl, n is 1 or 2 provided that when n is 2 at least two R groups are hydrogen, and x is the degree of polymerization resulting in a fiber forming polymer.

The polymer is conveniently prepared from highly purified monomer, i.e., monomer of at least about 98 percent purity, having the formula:

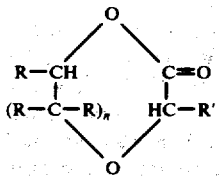

wherein R, R' and n are as defined above. When n is 1, the monomer is preferably p-dioxanone, methyl-p-dioxanone, or dimethyl-p-dioxanone. When n is 2, the monomer is preferably 1,4-dioxepan-2-one.

A particularly preferred monomer is p-dioxanone, and the following description and examples which are presented by way of illustration are directed primarily to the preparation and polymerization of that monomer, it being understood that certain variations may apply to other monomers and polymers encompassed by the above formula as will be readily apparent to those skilled in the art. Para-dioxanone monomer is conveniently prepared by reacting ethylene glycol, metallic sodium, and chloroacetic acid as hereinafter described in detail. The resulting monomer is preferably purified to 99+% purity by multiple distillations and recrystallizations. We have discovered that high monomer purity is necessary to obtain a high molecular weight polymer and ultimately, a fiber of good tensile and dry knot strength.

The purified monomer is polymerized at a temperature of 20° to 130° C, most preferably above 75° C, in the presence of an organometallic catalyst as hereinafter described in detail to obtain a high molecular weight polymer of p-dioxanone characterized by an inherent viscosity of at least about 0.50 measured as a 0.1% solution in tetrachloroethane at 25° C, and a crystallinity of at least about 20% as determined by X-ray diffraction.

The polymer is melt extruded through a spinneret in a conventional manner to form one or more filaments which are subsequently drawn about 4x to 6x in order to achieve molecular orientation and improve tensile properties. The resulting oriented filaments have good tensile and dry knot strength and good in vivo strength retention.

To further improve dimensional stability and tensile strength retention, the oriented filaments may be subjected to an annealing treatment. This optional annealing treatment consists of heating the filaments to a temperature of from about 50° to 105° C, most preferably from about 50° to 80° C while restraining the filaments to prevent any substantial shrinkage. The filaments are held at the annealing temperature for a few seconds to several days or longer depending on the temperature and processing conditions. In general, annealing at 50° to 80° C for up to about 24 hours is satisfactory for p-dioxanone. Optimum annealing time and temperature for maximum improvement in fiber in vivo strength retention and dimensional stability is readily determined for each fiber composition.

Since the function of a suture is to join and hold severed tissue until healing is well along, and to prevent separation as a result of movement or exercise, a suture must meet certain minimum standards of strength. It is particularly important that strength be maintained when knots are tied and during the actual procedure of drawing tight a suitable knot. Oriented filaments of the present invention are characterized by a straight tensile strength of at least about 40,000 psi and a knot strength of at least about 30,000 psi, although significantly higher strengths are possible as will be apparent from the following examples.

The preparation of high molecular weight oriented filaments of poly-p-dioxanone and other polymers of the present invention is further illustrated by the following examples where all percentages are by weight unless otherwise noted.

EXAMPLE I

A. Preparation of p-dioxanone

Metallic sodium is dissolved in a large excess of ethylene glycol to obtain a glycolate which is further reacted with about 0.5 mols of chloroacetic acid per mole of sodium to yield the sodium salt of the hydroxy acid. Excess ethylene glycol and by-products of the reaction are removed by distillation and by washing with acetone. The sodium salt is converted to the free hydroxy acid by the addition of hydrochloric acid, and the resulting sodium chloride is removed by precipitation with ethanol followed by filtration.

The hydroxy acid filtrate is slowly heated up to about 200° C, preferably in the presence of $MgCO_3$, to remove alcohol and water by distillation. Upon further heating at atmospheric pressure the p-dioxanone is formed and distills over at a head temperature of between about 200°–220° C. The purity of the crude dioxanone product is generally about 60–70 percent as determined by gas chromatography and yields are in the order of 50 to 70 percent.

The crude p-dioxanone is further purified to about 98 percent by redistillation, and finally purified to 99+% by multiple crystallizations and/or distillation.

B. Polymerization of p-dioxanone

Highly purified p-dioxanone is polymerized in the presence of an organometallic catalyst such as diethyl zinc or zirconium acetylacetonate to obtain high molecular weight, fiber forming polymers according to the following typical procedure.

0.1 M (10.2 g) of dry, 99+% pure p-dioxanone monomer is weighed into a dry flask under an inert atmosphere of dry nitrogen and 0.36 ml of 0.138M diethyl zinc in heptane are added. The monomer to catalyst ratio is calculated as 2000 : 1. After completely mixing the catalyst and monomer, the flask is swirled at intervals over a period of about one hour or less at room temperature until initiation and polymerization is evident by the occurrence of gelation. The flask is then connected to a vacuum of about 14 inches of Hg. The sealed flask is maintained at 80° C in a constant temperature bath for about 72 hours to complete the polymerization. The resulting polymer is characterized by an inherent viscosity I.V. of 0.70 measured on a 0.1% solution of polymer in tetrachloroethane at 25° C, a glass transition temperature $T_g$ of −16° C, a melting temperature $T_m$ of 110° C, and a crystallinity of 37 percent.

In the polymerization procedure, the initial one hour hold time for polymerization initiation is required only when using volatile catalysts which would be lost if the polymerization mixture was immediately placed under vacuum. When nonvolatile catalysts such as zirconium acetyl acetonate are used, this hold time may be omitted and the polymerization reaction mixture placed under vacuum immediately following addition and mixing of catalyst. As a further alternative, the entire polymerization reaction may be conducted under an inert atmosphere at atmospheric pressure.

C. Polymer Extrusion

The polymer obtained in the preceding step is thoroughly dried and melt extruded through a spinnerette using conventional textile fiber spinning procedures to obtain one or more continuous monofilament fibers suitable for use as synthetic absorbable sutures. The spun filaments are drawn about 5x at a temperature of about 43° C to increase molecular orientation and enhance physical properties, particularly tensile strength. The drawn monofilaments having a diameter of about 11 mils corresponding to a size 2-0 suture are characterized by an inherent viscosity of 0.64, a crystallinity of 30 percent, a straight tensile strength of 36,600 psi, an elongation of 99.4 percent, and a knot strength of 31,900 psi.

EXAMPLE II

The method of Example I was repeated using 0.13 ml of zirconium acetyl acetonate catalyst (7500 : 1 monomer to catalyst ratio) in the polymerization reaction. Properties of polymer and fiber were as follows:

Polymer
I.V.: 0.71
Tg: −16° C
Tm: 111° C
Crystallinity: 49%

Fiber
I.V.: 0.57
Tensile Strength: 38,600 psi
Elongation: 88.5 percent
Knot Strength: 32,300 psi

EXAMPLE III

Polydioxanone polymers were prepared in accordance with the polymerization method of Example I using 0.20 ml of zirconium acetyl acetonate catalyst (5000 : 1 monomer to catalyst ratio) and a polymerization temperature of 90° C. Polymer properties were as follows:
I.V.: 0.65
Tg: −19° C
Tm: 109° C
Crystallinity: 35%

EXAMPLE IV

The method of Example III was repeated using 0.50 ml of zirconium acetylacetonate catalyst. (2000 : 1 monomer to catalyst ratio). Polymer properties were as follows:
I.V.: 0.59
Tg: −17° C
Tm: 111° C
Crystallinity: 44%

EXAMPLE V

The method of Example I was repeated at a monomer to catalyst ratio of 4000 : 1 and with a polymerization reaction of three days at 80° C. The resulting polymer had an inherent viscosity of 0.86 and crystallinity of 30 percent. Fibers extruded from the polymer and drawn 6x at 87° C had a diameter of 9 mils, a straight tensile strength of 65,100 psi, elongation of 47.6%, and knot strength of 46,400 psi.

EXAMPLE VI

The method of Example I was repeated using tetraoctylene glycol titanate as the polymerization catalyst. The monomer to catalyst ratio was 12,300 : 1 based on titanium content, and the polymerization reaction was maintained at 80° C for six days. The resulting polymer had an inherent viscosity of 0.86 and a crystallinity of 33 percent. Extruded filaments drawn 6x at 83° C had a diameter of 11 mils, a tensile strength of 55,600 psi, a dry knot strength of 48,800 psi, and a Young's modulus of 167,000 psi.

EXAMPLE VII

Two lots of polydioxanone were prepared according to the method of Example VI using a monomer to catalyst ratio of 26,700 : 1 and with a polymerization reaction of six days and 12 days. The resulting polymers had inherent viscosities of 0.81 and 0.84 respectively. The polymers were combined and extruded into fiber which, after drawing 6x, had the following physical properties.
Fiber Diameter: 9 mils
Tensile Strength: 70,600 psi
Elongation: 46.3
Dry Knot Strength: 50,300 psi
The monofilament fibers had a high degree of softness and pliability.

EXAMPLE VIII

In Vivo Absorption

Two 2 cm segments of monofilament fiber from Example I having a diameter corresponding to size 2–0 suture were implanted aseptically into the left gluteal muscles of 24 female Long Evans rats. The implant sites were recovered after periods of 60, 90, 120 and 180 days and examined microscopically to determine the extent of absorption.

After 60 days the suture cross sections were still transparent and intact. The tissue reactions were slight and most sutures were encapsulated with fibrous tissue. The sutures at this period remained birefringent under polarized light.

At 90 days the sutures were becoming translucent and had lost some of their birefringent properties. A few of the suture cross sections stained pink (eosinophilic) around the periphery and the edges were indistinct, indicating the onset of absorption. The tissue reactions generally consisted of a fibrous capsule and a layer of macrophages interposed between it and the suture surface.

At 120 days the sutures were translucent, most cross sections had taken on an eosinophilic stain, and the sutures appeared to be in the process of active absorption. The tissue reactions consisted of an outer layer of fibroblasts with an interface of macrophages several cell layers thick. Absorption at 120 days was estimated to be approximately 70 percent complete.

At 180 days, absorption of the suture was substantially complete. The incision healed with minimal adverse tissue reaction.

EXAMPLE IX

In Vivo Strength Retention

Segments of the sutures of several Examples were implanted in the posterior dorsal subcutis of female Long Evans rats for periods of 14, 21 and 28 days. The sutures were recovered at the designated periods and tested for straight tensile strength with the following results.

| Test | Fiber | Implantation Time Days | Tensile Strength Pounds | Strength Retention % |
|---|---|---|---|---|
| a) | EX. I - | 0 | 3.37 | |
| | | 14 | 1.46 | 43.4 |
| | | 21 | 1.14 | 33.8 |
| | | 28 | — | — |
| b) | EX. I - (Sterilized)[1] | 0 | 3.08 | |
| | | 14 | 1.16 | 37.6 |
| | | 21 | 0.97 | 31.4 |
| | | 28 | 0.70 | 22.9 |
| c) | EX. VI - (Unannealed) | 0 | 3.47 | |
| | | 14 | 2.27 | 65.3 |
| | | 21 | 1.62 | 46.7 |
| | | 28 | 1.53 | 44.1 |
| d) | EX. VI - (Annealed)[2] | 0 | 6.47 | |
| | | 14 | 5.39 | 83.3 |
| | | 21 | 4.87 | 75.3 |
| | | 28 | 4.30 | 66.5 |
| e) | EX. VI - (Annealed)[2,3] | 0 | 3.82 | |
| | | 14 | 2.07 | 54.0 |
| | | 21 | 1.36 | 35.5 |
| | | 28 | 0.68 | 17.8 |
| f) | EX. V - (Sterilized)[1] | 0 | 4.05 | |
| | | 14 | 2.77 | 68.4 |
| | | 21 | 2.40 | 59.3 |
| | | 28 | 2.15 | 53.2 |
| g) | EX. V - (Sterilized)[3] | 0 | 3.45 | |
| | | 14 | 2.11 | 61.3 |
| | | 21 | 1.36 | 39.3 |
| | | 28 | 0.92 | 26.6 |

[1]Sterilized with ethylene oxide at 30° C.
[2]Annealed under nitrogen 24 hours at 65° C.
[3]Sterilized with cobalt 60.

EXAMPLE X

Small quantities of polydioxanone polymer were prepared in accordance with the general method of Example I using chromatographically pure p-dioxanone monomer and diethyl zinc and tetraoctylene glycol titanate as catalysts. Polymer prepared with diethyl zinc catalyst at a monomer to catalyst ratio of 4,000 and with a polymerization reaction of three days at 80° C had an inherent viscosity of 1.18. Polymer prepared with tetraoctylene glycol titanate catalyst at a monomer to catalyst ratio of 12,250 and with a polymerization reaction of 6 days at 80° C had an inherent viscosity of 1.15. A second batch of high purity p-dioxanone monomer twice distilled in an annular still under a vacuum of 0.10–0.15 mm Hg was polymerized in the presence of tetraoctylene glycol titanate catalyst at a monomer to catalyst ratio of 13,300 and at 80° C for 6 days. The resulting polymer had an inherent viscosity of 2.26.

EXAMPLE XI

Preparation of Methyl-p-Dioxanone

Following the general procedure of Example I,, metallic sodium was dissolved in a large excess of 1,2-propane diol and chloroacetic acid was added at 110°–115° C. Excess diol was removed by distillation and the sodium salt of the hydroxy acid converted to free acid by the addition of water and hydrochloric acid. Sodium chloride was precipitated by the addition of ethanol and removed by filtration. The resulting product was distilled in the presence of $M_gCO_3$ to remove excess alcohol and water and to recover crude methyl dioxanone monomer as a distillate at 196° to 202° C. After purification, the monomer can be polymerized and extruded to form fibers suitable for use as absorbable sutures as described in Example I.

EXAMPLE XII

Preparation of Dimethyl-p-Dioxanone

The procedure of Example XI was repeated reacting metallic sodium with 2,3-butanediol and choroacetic acid at about 130° C. Crude dimethyl dioxanone monomer was recovered from the distillation at 190° to 213° C. After purification the monomer can be polymerized and extruded to form fibers suitable for use as absorbable sutures as described in Example I.

EXAMPLE XIII

Preparation of 1,4-dioxepan-2-one

The procedure of Example VI was repeated reacting metallic sodium with 1,3-propane diol and chloroacetic acid. Crude 1,4-dioxepan-2-one monomer was recovered from the distillation at 300° to 310° C. After purification, the monomer can be polymerized and extruded to form fibers suitable for use as absorbable sutures as described in Example I.

We have discovered that exceptionally high purity of p-dioxanone monomer is required to obtain polymers having a sufficiently high inherent viscosity to yield strong fibers upon extrusion. In general, the monomers are purified to 99+% by distillation and recrystallization prior to polymerization, and the resulting polymers have an inherent viscosity of at least about 0.50, and preferably 0.80 or higher measured as above described. As illustrated in Example X, polymers prepared from highly purified dioxanone have inherent viscosities well in excess of 1.10.

Drawn fibers of polydioxanone possess an unique combination of desirable properties. In particular, the monofilament fibers combine high tensile strength and knot strength with a pliability not to be found in any previous absorbable suture material, natural or synthetic. For example, the Young's modulus of the polydioxanone fiber of Example VI was 167,200 psi. In comparison, the Young's modulus for monofilament polyglycolide fibers and for 90/10 glycolide/lactide copolymer fibers is about 1 - 2 million psi, while that for moist catgut is about 350,000 psi. The low Young's modulus of polydioxanone makes this fiber particularly well suited for use as an absorbable monfilament suture, whereas prior synthetic absorbable sutures have largely been limited to braided, multifilament constructions which tend to be softer and more flexible than corresponding sizes of monofilament material. Monofilamented sutures are, of course, preferred for use in many surgical applications such as in ophthalmic procedures where smoothness of the suture surface is of particular importance.

The polymers of p-dioxanone of the present invention are also unique as compared with prior synthetic absorbable materials in that the sutures of these polymers can be sterilized by cobalt 60 radiation as well as by ethylene oxide. As illustrated in Example IX, while cobalt 60 sterilization results in some reduction in fiber strength and some increase in the in vivo rato of strength loss, the sterilized fiber nevertheless retains sufficient strength initially and for 28 days in vivo to make the fiber suitable for use in surgical procedures.

While the preceding examples have been directed to the preparation of homopolymers of p-dioxanone, methyl dioxanone, dimethyl dioxanone, and 1,4-dioxepan-2-one, these examples are for purposes of illustration only and are not limiting of the invention. Mixtures of these polymers, copolymers of two or more of the above enumerated monomers, and copolymers of these monomers with up to about 50% by weight of other copolymerizable monomers which produce non-toxic and absorbable polymers are likewise included within the present invention. For example, such copolymers of dioxanone with lactide and/or glycolide are useful in the preparation of absorbable sutures, and the physical and chemical properties of such sutures such as strength, stiffness, and rate of absorption can be controlled by varying the relative proportions of the monomer constituents. In addition, the copolymers may be prepared by random, block or graft polymerization techniques in order to obtain particular combinations of compositions and physical and chemical properties. In certain applications where the rate of absorption of polydioxanone is less than desired, copolymers of dioxanone with from about 5 to 25 percent or more glycolide having a faster rate of absorption may be preferred.

It is to be understood that inert additives such as coloring materials and plasticizers can be incorporated in the sutures. Any of a variety of plasticizers such as, for instance, glyceryl triacetate, ethyl benzoate, diethyl phthalate, dibutyl phthalate and bis 2-methoxyethyl phthalate can be used if desired. The amount of plasticizer may vary from 1 to about 20 percent or more based on the weight of the polymer. Not only does the plasticizer render the filaments even more pliable, but it also helps in spinning. As used herein, the term "inert" means materials that are chemically inert to the polymer, and biologically inert to living tissue, i.e., do not cause any of the adverse effects previously discussed.

Filaments of the present invention are adversely affected by moisture and are accordingly preferably packaged in a substantially moisture free environment and in hermetically sealed packages, a preferred form of which is shown in FIG. 2. In FIG. 2, there is shown a suture package 14 having disposed therein a coil of suture 12, one end of which is attached to needle 13. The needle and suture are positioned within a cavity 16 that is evacuated or filled with a dry atmosphere such as air or nitrogen. The package is fabricated of two sheets of aluminum foil or an aluminum foil-plastic laminate and heat sealed or bonded with adhesive at the skirt 16 to hermetically seal the cavity and isolate the contents of the package from the external atmosphere.

Filaments of the present invention may be used as monofilament or multifilament sutures, or may be woven, braided, or knitted either alone or in combination with absorbable fibers such as polyglycolide or poly (lactide-co-glycolide), or with non-absorbable fibers such as nylon, polypropylene, polyethyleneterephthalate, or polytetrafluoroethylene to form multifilament sutures and tubular structures having use in the surgical repair of arteries, veins, ducts, esophagi and the like.

Multifilament yarns that contain polymer filaments of the present invention together with nonabsorbable filaments are illustrated in FIG. 4 wherein the nonabsorbable fiber is represented by the hatched fiber cross section 19. In FIG. 4, the fibers 20 are extruded from homopolymer or copolymer compositions of the present invention as described above. The relative proportions of absorbable filaments 20 and nonabsorbable filaments 19 may be varied to obtain the absorption characteristic desired in the woven fabric or tubular implants. Methods of weaving and crimping vascular prostheses are described in U.S. Pat. 3,096,560.

Composite fabrics of absorbable and nonabsorbable materials fashioned by textile processes including weaving, knitting, and fabricating by the nonwoven felting of fibers are described in U.S. Pat. No. 3,108,357 and U.S. Pat. No. 3,463,158. Similar techniques may be used in the manufacture of surgical aids wherein nonabsorbable fibers are combined with absorbable fibers composed of the polymers of this invention. The surgical utility of "bicomponent filaments" containing absorbable and nonabsorbable components is described in U.S. Pat. No. 3,463,158, the teaching of which is incorporated herein by reference. Monofilaments of the polymers of the present invention may be woven or knitted to form an absorbable fabric having the structure illustrated in FIG. 5, useful surgically in hernia repair and in supporting damaged liver, kidney, and other internal organs.

The products of the invention are useful in surgical applications where an absorbable aid or support is required, as for example, in the formation of surgical mesh, absorbable staples, artifical tendons, or cartilage material, and in other uses where a temporary aid during healing is needed. They may also be used to advantage in repairing hernias and in anchoring organs which have become loose.

The polymers of the present invention are also useful in the manufacture of cast films and other solid surgical aids such a scleral buckling prostheses. Thus, cylindrical pins, screws as illustrated in FIG. 3, reinforcing plates, etc., may be machined from the cast polymer having in vivo absorption characteristics depending upon the polymer composition and molecular weight.

Many different embodiments of this invention will be apparent to those skilled in the art and may be made without departing from the spirit and scope thereof. It is accordingly understood that this invention is not limited to the specific embodiments thereof except as defined in the appended claims.

We claim:

1. A sterile, synthetic absorbable suture comprising oriented fiber of a polymer of a monomer having the formula:

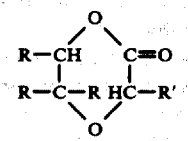

wherein R' and R are individually hydrogen, methyl or ethyl, said suture being dry to the extent of being substantially free of moisture, and characterized by a Young's modulus of less than about 600,000 psi with a correspondingly high degree of softness and flexibility, an initial straight tensile and knot strength of at least about 40,000 psi and 30,000 psi respectively, and substantially complete absorption in vivo within about 180 days.

2. A suture of claim 1 wherein R and R' are hydrogen and the monomer is p-dioxanone.

3. A suture of claim 2 wherein said polymer is characterized by an inherent viscosity greater than about 0.50 measured as 0.1% solution of polymer in tetrachloroethane at 25° C.

4. A suture of claim 3 comprising a homopolymer of p-dioxanone.

5. A suture of claim 1 comprising a polymer of methyl-p-dioxanone.

6. A suture of claim 1 comprising a polymer of dimethyl-p-dioxanone.

7. A suture of claim 1 comprising a copolymer of more than 50% by weight p-dioxanone and less than 50% by weight of at least one other monomer copolymerizable with p-dioxanone to an absorbable polymer.

8. A suture of claim 7 wherein said copolymer is of p-dioxanone and glycolide or lactide.

9. A sterile synthetic absorbable suture comprising oriented fiber of a polymer having units of the formula:

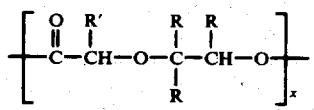

wherein R' and R are individually hydrogen, methyl, or ethyl and x is the degree of polymerization resulting in a fiber forming polymer, said suture being dry to the extent of being substantially free of moisture, and characterized by a Young's modulus of less than about 600,000 psi with a correspondingly high degree of softness and flexibility, an initial straight tensile and knot strenght of at least about 40,000 psi and 30,000 psi respectively, and substantially complete absorption in vivo within about 180 days.

10. A suture of claim 9 wherein said polymer is a homopolymer of p-dioxanone having an inherent viscosity of at least 0.50 in a 0.1% solution of tetrachloroethane at 25° C.

11. A suture of claim 10 wherein the inherent viscosity of said polymer is at least 0.80.

12. A suture of claim 9 wherein said polymer is a copolymer of more than 50% by weight p-dioxanone with less than 50% by weight of at least one other monomer copolymerizable to an absorbable polymer.

13. A suture of claim 12 wherein said polymer is a copolymer of p-dioxanone and lactide or glycolide.

14. A suture of claim 9 wherein said polymer is a homopolymer of methyl-p-dioxanone or copolymer of more than 50% by weight methyl-p-dioxanone with less than 50% by weight of at least one other monomer copolymerizable to an absorbable polymer.

15. A suture of claim 9 wherein said polymer is a homopolymer of dimethyl-p-dioxanone or copolymer of more than 50% by weight dimethyl-p-dioxanone with less than 50% by weight of at least one other monomer copolymerizable to an absorbable polymer.

16. A suture of claim 1 having a surgical needle attached to at least one end thereof.

17. A needle and suture combination of claim 16 packaged in a sterile and dry environment within a hermetically sealed and substantially moisture impervious container.

18. A suture of claim 9 having a surgical needle attached to at least one end thereof.

19. A needle and suture combination of claim 18 packaged in a sterile and dry environment within a hermetically sealed and substantially moisture impervious container.

20. A surgical prosthesis comprising a fabric manufactured at least in part from synthetic absorbable fibers of a polymer having units of the formula:

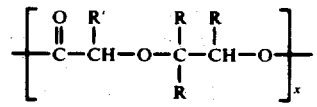

wherein R' and R are individually hydrogen, methyl, or ethyl and x is the degree of polymerization resulting in a fiber forming polymer, said fibers being dry to the extent of being substantially free of moisture, and characterized by a Young's modulus of less than about 600,000 psi with a correspondingly high degree of softness and flexibility, an initial straight tensile and knot strength of at least about 40,000 psi and 30,000 psi respectively, and substantially complete absorption in vivo within about 180 days.

21. A surgical prosthesis of claim 20 wherein said polymer is a homopolymer of p-dioxanone or a copolymer of more than 50% by weight p-dioxanone with less than 50% by weight of at least one other monomer copolymerizable to an absorbable polymer.

22. A surgical prosthesis of claim 20 wherein said polymer is a homopolymer of methyl-p-dioxanone or a copolymer of more than 50% by weight methyl-p-dioxanone with less than 50% by weight of at least one other monomer copolymerizable to an absorbable polymer.

23. A surgical prosthesis of claim 20 wherein said polymer is a homopolymer of dimethyl-p-dioxanone or a copolymer of more than 50% by weight dimethyl-p-dioxanone with less than 50% by weight of at least one other monomer copolymerizable to an absorbable polymer.

24. A surgical prosthesis comprising a solid surgical aid formed from an absorbable polymer having units of the formula:

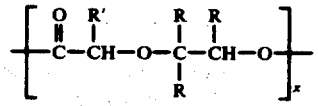

wherein R' and R are individually hydrogen, methyl, or ethyl and x is the degree of polymerization resulting in a fiber forming polymer, said prosthesis being dry to the extent of being substantially free of moisture.

25. A surgical prosthesis of claim 24 wherein said polymer is a homopolymer of p-dioxanone having an inherent viscosity of at least 0.50 in a 0.1% solution of tetrachloroethane at 25° C.

26. A surgical prosthesis of claim 24 wherein said polymer is a copolymer of at least 50% by weight p-dioxanone with less than 50% by weight of at least one other monomer copolymerizable to an absorbable polymer.

27. A surgical prosthesis of claim 24 wherein said polymer is a homopolymer of methyl-p-dioxanone or acopolymer of more than 50% by weight methyl-p-dioxanone with less than 50% by weight of at least one other monomer copolymerizable to an absorbable polymer.

28. A surgical prosthesis of claim 24 wherein said polymer is a homopolymer of dimethyl-p-dioxanone or a copolymer of more than 50% by weight dimethyl-p-dioxanone with less than 50% by weight of at least one other monomer copolymerizable to an absorbable polymer.

29. A method of closing a wound in living tissue which comprises approximating the edges of the wound with a synthetic absorbable suture consisting of at least one filament of a polymer of a monomer having the formula:

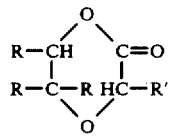

wherein R' and R are individually hydrogen, methyl or ethyl, said suture being at least partially embedded in the living tissue, and leaving said suture in said tissue until the embedded suture is absorbed during the healing process, said suture being characterized by a Young's modulus of less than about 600,000 psi with a correspondingly high degree of softness and flexibility, an initial straight tensile and knot strength of at least about 40,000 psi and 30,000 psi respectively, and substantially complete absorption in vivo within about 180 days.

30. A method of claim 29 wherein R and R' are hydrogen and the monomer is p-dioxanone.

31. A method of claim 29 wherein the monomer is methyl-p-dioxanone.

32. A method of claim 29 wherein the monomer is dimethyl-p-dioxanone.

33. A method of closing a wound in living tissue which comprises approximating the edge of the wound with a synthetic absorbable suture consisting of at least one filament of a polymer having units of the formula:

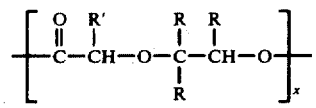

wherein R' and R are individually hydrogen, methyl or ethyl, and x is the degree of polymerization resulting in a fiber forming polymer, said suture being at least partially embedded in the living tissue, and leaving said suture in said tissue until the embedded suture is absorbed during the healing process, said suture being characterized by a Young's modulus of less than about 600,000 psi with a correspondingly high degree of softness and flexibility, an initial straight tensile and knot strength of at least about 40,000 psi and 30,000 psi respectively, and substantially complete absorption in vivo within about 180 days.

34. A method of claim 33 wherein said polymer is a homopolymer of p-dioxanone having an inherent viscosity of at least 0.50 in a 0.1 percent solution of tetrachloroethane at 25° C.

35. A method of claim 34 wherein the inherent viscosity of said polymer is at least 0.80.

36. A method of claim 33 wherein said polymer is a copolymer of more than 50% by weight p-dioxanone with less than 50% by weight of at least one other monomer copolymerizable to an absorbable polymer.

37. A method of claim 36 wherein said polymer is a copolymer of p-dioxanone and lactide or glycolide.

38. A method of claim 33 wherein said polymer is a homopolymer of methyl-p-dioxanone or a copolymer of more than 50% by weight methyl-p-dioxanone with less than 50% by weight of at least one other monomer copolymerizable to an absorbable polymer.

39. A method of claim 33 wherein said polymer is a homopolymer of dimethyl-p-dioxanone or a copolymer of more than 50% by weight dimethyl-p-dioxanone with less than 50% by weight of at least one other monomer copolymerizable to an absorbable polymer.

* * * * *